United States Patent
Kleeman et al.

(10) Patent No.: US 9,754,083 B2
(45) Date of Patent: Sep. 5, 2017

(54) AUTOMATIC CREATION OF CLINICAL STUDY REPORTS

(71) Applicant: ClinGenuity, LLC, Cincinnati, OH (US)

(72) Inventors: Keith M. Kleeman, Cincinnati, OH (US); Mickey W. Kowitz, Maineville, OH (US)

(73) Assignee: Clingenuity, LLC, Cincinnati, OH (US)

( * ) Notice: Subject to any disclaimer, the term of this patent is extended or adjusted under 35 U.S.C. 154(b) by 495 days.

(21) Appl. No.: 14/353,513

(22) PCT Filed: Oct. 24, 2012

(86) PCT No.: PCT/US2012/061570
§ 371 (c)(1),
(2) Date: Apr. 23, 2014

(87) PCT Pub. No.: WO2013/063029
PCT Pub. Date: May 2, 2013

(65) Prior Publication Data
US 2014/0316822 A1    Oct. 23, 2014

Related U.S. Application Data

(60) Provisional application No. 61/550,955, filed on Oct. 25, 2011.

(51) Int. Cl.
*G06Q 50/22*        (2012.01)
*G06F 19/00*        (2011.01)
(Continued)

(52) U.S. Cl.
CPC ........ *G06F 19/363* (2013.01); *G06F 17/2247* (2013.01); *G06F 17/30321* (2013.01);
(Continued)

(58) Field of Classification Search
CPC .... G06F 19/322; G06F 19/345; G06F 17/274; G06F 19/326; G06F 19/3487;
(Continued)

(56) References Cited

U.S. PATENT DOCUMENTS

| | | |
|---|---|---|
| 6,006,225 A | 12/1999 | Bowman et al. |
| 2002/0046235 A1 | 4/2002 | Foy et al. |

(Continued)

OTHER PUBLICATIONS

International Bureau, International Preliminary Report on Patentability, PCT/US2012/061570, May 8, 2014, 7 pgs.

(Continued)

*Primary Examiner* — Maroun Kanaan
(74) *Attorney, Agent, or Firm* — Lewis Rice LLC

(57) ABSTRACT

An apparatus (102, 104) and method for generating a formatted clinical study report (206) by analyzing submitted clinical study data (150) based on semantics and maximum entropy analysis at a server (104). Sections of the formatted clinical study report are identified in the submitted data (111) using semantics analysis and maximum entropy analysis (204). The identified sections are formatted and output as the formatted clinical study report (206). The formatted clinical study report (206) may be reviewed and edited after generation by a user interfacing with the server (104).

12 Claims, 8 Drawing Sheets

(51) Int. Cl.
   *G06F 17/22*    (2006.01)
   *G06Q 50/24*    (2012.01)
   *G06Q 10/00*    (2012.01)
   *G06F 17/30*    (2006.01)

(52) U.S. Cl.
   CPC ....... *G06F 17/30522* (2013.01); *G06Q 10/00* (2013.01); *G06Q 50/22* (2013.01)

(58) Field of Classification Search
   CPC ............. G06F 17/2785; G06F 19/3443; G06F 17/2715; G06F 17/30401; G06F 17/30684; G06F 17/30654; G06N 99/005; G06Q 50/22; G06Q 50/24
   See application file for complete search history.

(56) References Cited

U.S. PATENT DOCUMENTS

| | | |
|---|---|---|
| 2003/0036923 A1 | 2/2003 | Waldon et al. |
| 2006/0293919 A1 | 12/2006 | Morlet et al. |
| 2014/0164023 A1* | 6/2014 | Yegnanarayanan ... G06F 19/322 705/3 |

OTHER PUBLICATIONS

Bashyam et al., "Identifying Anatomical Phrases in Clinical Reports by Shallow Semantic Parsing Methods". In Proceedings of the 2007 IEEE Symposium on Computational Intelligence and Data Mining (CIDM 2007) [online]. [retrieved on Dec. 13, 2012] Retrieved from the Internet <URL: http://vbashyam.bol.ucla.edu/publications/Bashyam-CIDM2007.PDF> entire document, expecially Abstract; p. 211, p. 213 (5 pgs.).

* cited by examiner

AUTOMATIC CREATION OF CLINICAL STUDY REPORTS

CROSS REFERENCE TO RELATED APPLICATIONS

This application claims priority to U.S. Provisional Application Ser. No. 61/550,955 filed on Oct. 25, 2011, and PCT Application No. PCT/US2012/061570, filed Oct. 24, 2012 and published as WO 2013/063029, each of which is hereby incorporated by reference in its entirety.

BACKGROUND

A clinical trial (also referred to as an "interventional study") generally corresponds to a series of tests for medical research and/or drug development that collects large amounts of data related to the medical research and/or drug development. After completion of a clinical trial, the data and findings may be compiled and a clinical study report is created that includes protocol, statistical analysis plan and locked data reports. Conventionally, the protocol, statistical analysis plan, and locked data reports may be manually analyzed and formatted into the International Conference on Harmonisations' (ICH) E3 Guidelines for the Structure of the Clinical Study report, and the formatted clinical study report may be provided to the appropriate governmental agency for submission. Manual formatting and review of a clinical study report requires a significant investment of resources, including for example approximately four months of time.

The United States National Institutes of Health maintains a database of publicly and privately supported clinical studies (accessible at http://www.clinicaltrials.gov) that indicates approximately 130,000 clinical trials are registered for the database. As such, the significant time delay and cost of formatting clinical studies for submission is an increasingly important problem.

Therefore, a significant need continues to exist in the art for improved systems and methods for the generation and review of formatted clinical study reports.

SUMMARY OF THE INVENTION

The invention addresses these and other problems associated with the prior art by analyzing submitted data based at least in part on semantics and formatting the submitted data to generate a formatted clinical study report. Moreover, the invention generates a user interface to facilitate review of the formatted clinical study report, where such user interface may be generated by a server and accessible by a user device communicating with the server.

It should be understood that the appended drawings are not necessarily to scale, presenting a somewhat simplified representation of various features illustrative of the basic principles of embodiments of the invention. The specific features consistent with embodiments of the invention disclosed herein, including, for example, specific dimensions, orientations, locations, sequences of operations and shapes of various illustrated components, will be determined in part by the particular intended application, use and/or environment. Certain features of the illustrated embodiments may have been enlarged or distorted relative to others to facilitate visualization and clear understanding.

DETAILED DESCRIPTION

Figure 1:
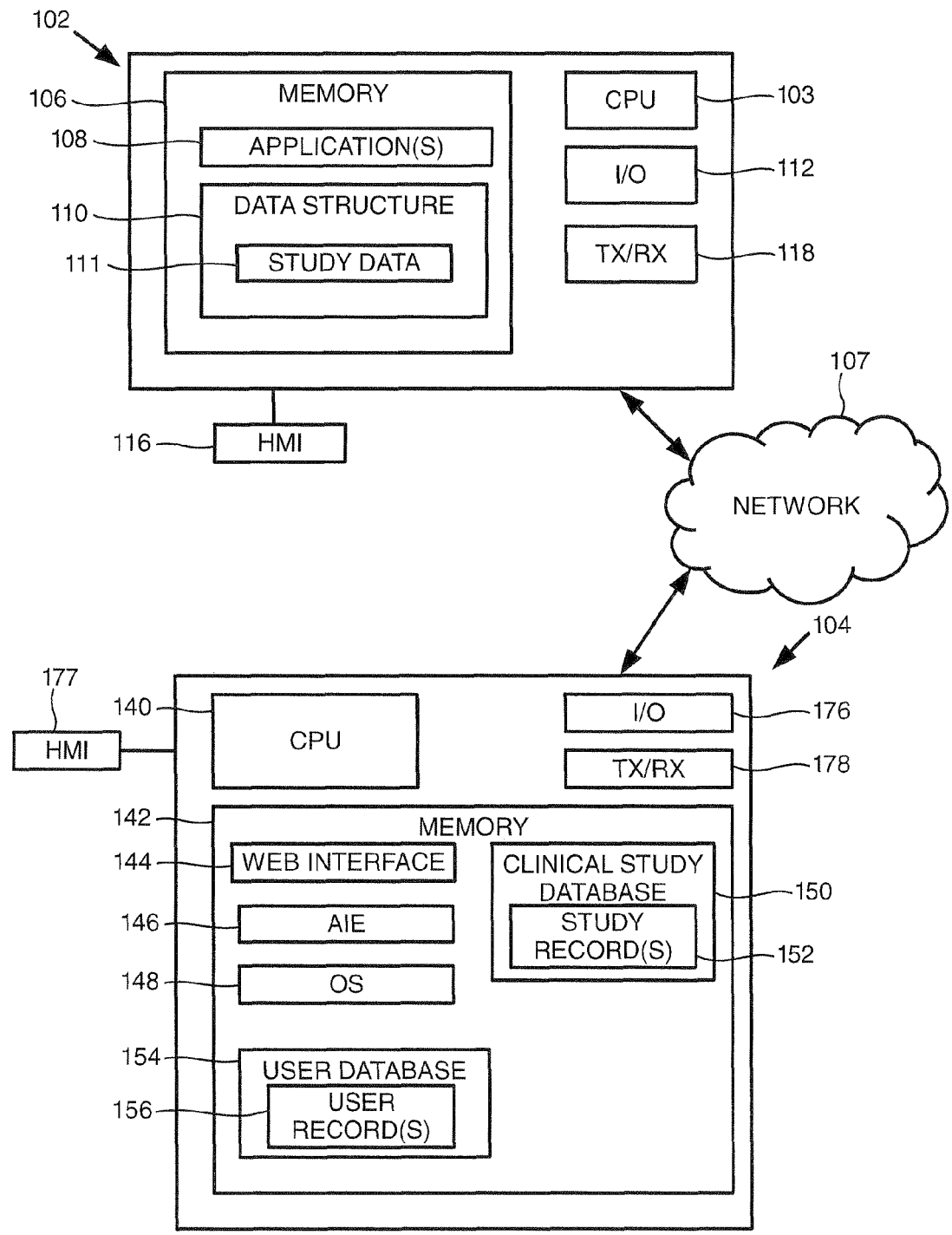
FIG. 1 is a block diagram illustrating components of a user device and clinical study server consistent with embodiments of the invention.

Turning to FIG. 1, this figure provides a block diagram of a user device 102 and a clinical study server 104 consistent with embodiments of the invention, where the user device 102 and clinical study server 104 may be in communication over a communication network 107. As shown, the user device 102 includes one or more processors (illustrated as 'CPU') 103 for executing one or more instructions to perform and/or cause components of the user device 102 to perform one or more operations consistent with embodiments of the invention. The user device 102 includes a memory 106, and at least one application 108 and a data structure 110 stored by the memory 106. The data structure may store data for a clinical study 111, which may be analyzed and formatted by embodiments of the invention to generate a formatted clinical study report. User device 102 further includes an input/output ("I/O") interface 112, and a human-machine interface ("HMI") 116.

The clinical study data 111 generally includes one or more data files corresponding to the clinical study, including for example one or more data files that include textual and/or graphical information related to the protocol used in the clinical study, one or more data files that includes textual and/or graphical information related to reports for the clinical study, and/or one or more data files that include textual and/or graphical information related to a statistical analysis plan for the clinical study. The one or more data files of the clinical study data 111 may be configured in a variety of file formats, including for example, Microsoft® Word, Excel, OpenXML, and/or PowerPoint file formats, Adobe® Acrobat Portable Document Format (PDF), unformatted text file format (e.g., '.txt' file format), hyper text markup language (HTML) file format, various image file formats, and/or other such data formats known to those skilled in the art having the benefit of the instant disclosure.

The at least one application 108 may generally comprise program code that when executed by the processor 103 facilitates interfacing between a user of the user device 102 and the clinical study server 103 over the communication network 107. Accordingly, a user may input data corresponding to a clinical study report, and the data may be transmitted to the clinical study server 104 for formatting to generate a formatted clinical study report which may be reviewed by the user using the user device 102 to interface with the clinical study server 104.

The memory 106 may represent random access memory (RAM) comprising the main storage of a computer, as well as any supplemental levels of memory, e.g., cache memories, non-volatile or backup memories (e.g., programmable or flash memories), mass storage memory, read-only memories (ROM), etc. In addition, the memory 106 may be considered in various embodiments of this invention to include memory storage physically located elsewhere, e.g., cache memory in a processor of any computing system in communication with the user device 102, as well as any storage device on any computing system in communication with the user device 102 (e.g., a remote storage database, a memory device of a remote computing device, cloud storage, etc.).

The I/O interface 112 of user device 102 may be configured to receive data from input sources and output data to output sources. For example, the I/O interface 112 may receive input data from a user input device such as a keyboard, mouse, microphone, touch screen, and other such user input devices, and the I/O interface 112 may output data to one or more user output devices such as a display (e.g., a computer monitor), a touch screen, speakers, and/or other such output devices that may be used to output data in a format understandable to a user. Such input and output devices are generally represented in FIG. 1 as the human-machine interface ("HMI") 116. As such, in some embodiments of the invention, user input data may be communicated to the processor 103 of the user device 102 using a user input device such as a keyboard or touch screen utilizing the HMI interface 116 and the I/O interface 112.

The user device 102 may include a network interface controller (Tx/Rx) 118 that is configured to transmit data over the communication network 107 and/or receive data from the communication network 108. For example, the physical connection between the network 107 and user device 102 may be supplied by a network interface card, an adapter, or a transceiver. As will be described herein, the user device 102 may communicate data over the communication network 107 to thereby interface with the clinical trial server 104, and such interfacing may be controlled by the processor 103 utilizing the network interface controller 118. For example, the processor 103 may execute application 108 which may be a web application that is downloaded from clinical study server 104 to thereby facilitate interfacing between the user device 102 and the clinical study server 104. As another example, the processor 103 may execute application 108 that comprises an internet browser that loads web pages communicated by the clinical study server 104 to thereby facilitate interfacing between the user device 102 and the clinical study server 104.

The clinical study server 104 may include one or more processors 140 configured to execute instructions to perform one or more operations consistent with embodiments of the invention. The clinical study server 104 may further include memory 142 accessible by the one or more processors 140. The memory 142 stores one or more applications, including a web interface application 144 and an artificial intelligence engine (AIE) 146, and/or an operating system 148. The applications 144, 146 and/or operating system 146 includes instructions in the form of program code that may be executed by the processor 140 to perform or cause to be performed one or more operations consistent with embodiments of the invention.

Generally, execution of the web interface application 144 and by the processor 140 may cause the clinical study server 104 to communicate with the user device 102 over the communication network 107 to thereby interface with the user device 102. The clinical study server may receive clinical study data from a user using the user device 102 during execution of the web interface application 144. After receiving the clinical study data, execution of the AIE 146 may cause the processor 140 to analyze the submitted clinical study data and format the data to generate a formatted clinical study report. The executing web interface application 144 may cause the processor 140 to interface with the user device 102 to allow the user of the user device 102 to review and edit the formatted clinical study report using the user device 102.

The memory 142 of the clinical study server 104 may include a data structure in the form of a clinical study database 150 that stores a plurality of clinical study records 152. Each clinical study record 152 corresponds to a particular clinical study and may store the clinical study data submitted for formatting, the formatted clinical study data, a user identification associated with the clinical study, and/or any other such data. Moreover, the memory 142 may further include a data structure in the form of a user database 154 that stores one or more user records 156. Each user record 156 corresponds to a user/entity that submits clinical study data for formatting, where the user record 156 may store one or more user identifications associated with the user record 156, a password for each user identification, contact information such as an email address, a telephone number, a mailing address and/or other such information, data indicating statistics associated with the clinical study data previously submitted and/or clinical study reports previously formatted for the user identification including for example template clinical study reports (i.e., historical data), and/or data indicating study records 152 associated with the user record 156.

As discussed above with respect to the user device 102, the memory 142 of the clinical study server 104 may represent local memory and/or remote memory. As such, while the memory 142 is illustrated as one component, the invention is not so limited. In some embodiments the memory 142 may comprise remote memory accessible to the processor 140 and located in one or more remote computing systems, including for example, one or more interconnected data servers accessible over one or more communication networks. Hence, while the web interface application 144, AIE 146, OS 148, clinical study database 150, and user database 154 are illustrated as located in memory 142 in clinical study server 104, in some embodiments, the web interface application 144, AIE 146, OS 148, clinical study database 150, and user database 154 may be physically located in memory of one or more remote memory locations accessible by the processor 140. The memory 142 may also include a database management system in the form of a computer program that, when executing as instructions on the processor 140, is used to access the information or data stored in the records of the clinical study database 150 and user database 154. The clinical study database 150 and user database 154 may be stored in any database organization and/or structure including for example relational databases, hierarchical databases, network databases, and/or combinations thereof.

The clinical study server 104 may further include an input/output ("I/O") interface 176, where the I/O interface 176 may be configured to receive data from input sources and output data to output sources. For example, the I/O interface 176 may receive input data from a user input device such as a keyboard, mouse, microphone, touch screen, and other such user input devices, and the I/O interface 176 may output data to one or more user output devices such as a computer monitor, a touch screen, speakers, and/or other such output devices that may be used to output data in a format understandable to a user. Such input and output devices are generally represented in FIG. 1 as an HMI 177. As such, in some embodiments of the invention, input data may be communicated to the processor 140 of the clinical study server 140 using a user input device such as a keyboard or touch screen utilizing the I/O interface 176. Furthermore, as discussed previously, in some embodiments, the clinical study server 104 may comprise a plurality of interconnected computing devices each located locally or remotely. As such, in these embodiments data may be input to the clinical study server via an HMI 177 and I/O interface 176 located remote from the computing device including a processor 140 and/or a memory 142. The clinical study server may include a network interface controller (Tx/Rx) 178, where data may be transmitted and/or received over the network 108 of FIG. 1 using each network connection device 178. For example, the physical connection between the network 108 and clinical study server 104 may be supplied by a network interface card, an adapter, or transceiver.

Figure 2:
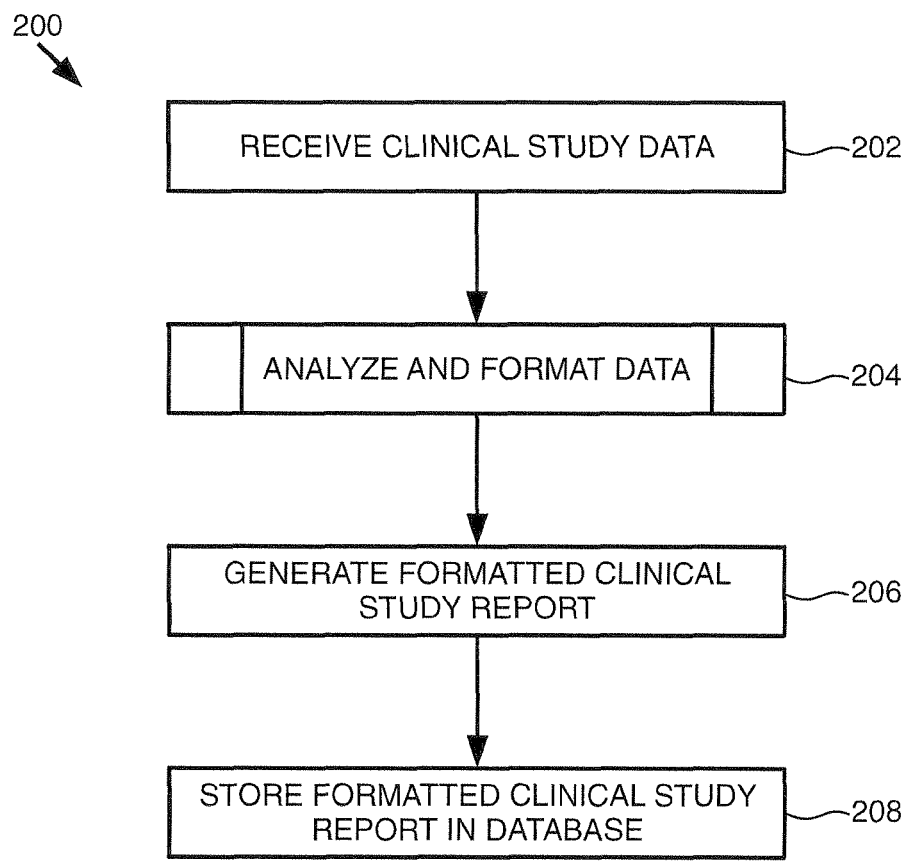
FIG. 2 is a flowchart illustrating a sequence of operations that may be performed by the clinical study server of FIG. 1.

FIG. 2 provides a flowchart 200 that illustrates a sequence of operations that may be performed by the processor 140 of the clinical study server 104 of FIG. 1 to generate a formatted clinical study report consistent with embodiments of the invention. The clinical study server 104 receives clinical study data from the user device 102 over the communication network 107 (block 202). The clinical study server 104 analyzes the clinical study data to identify sections of the files of the clinical study data and required elements for a clinical study report from the identified sections, and the clinical study server formats the sections of the clinical study data (block 204). The clinical study server generates a formatted clinical study report based at least in part on the formatted sections and identified required elements (block 206), and the formatted clinical study report is stored in a study record 152 corresponding to the clinical study in the clinical study database 150.

Figure 3:
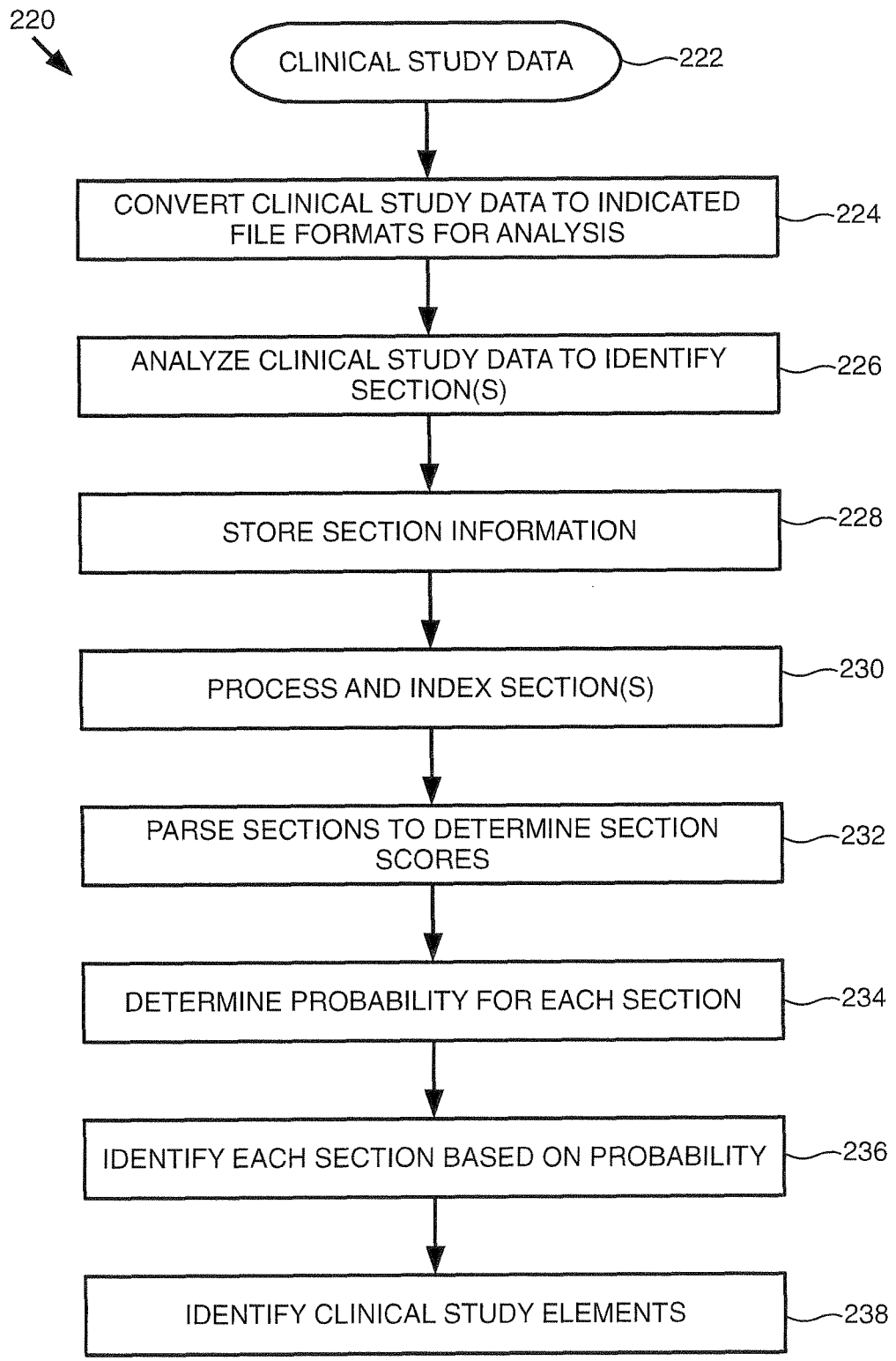
FIG. 3 is a flowchart illustrating a sequence of operations that may be performed by the clinical study server of FIG. 1.

FIG. 3 provides a flowchart 220 that illustrates a sequence of operations that may be performed by the processor 140 of the clinical study server 104 of FIG. 1 executing the AIE 146 to analyze and format clinical study data consistent with embodiments of the invention. The clinical study data is loaded for processing (block 222). The clinical study server 104 converts the various files included in the clinical study data to one or more file formats compatible with analysis by the AIE 146 (block 224). For example, the clinical study server 104 may convert the files of the clinical study data to a file format for analysis. For example, the clinical study server 104 may convert the files of the clinical study data to HTML.

The clinical study server 104 executing the AIE 146 analyzes the clinical study data to identify sections in the files of the clinical study data (block 226). For example, in some embodiments, the clinical study server 104 identifies sections in the files by locating each HTML heading level in each file of the clinical study data and maintains a relational record of each heading and corresponding parent and child sections. In addition, the clinical study server 104 executing the AIE 146 may replace HTML tags associated with the located HTML heading levels with an XML placeholder. After determining each section, the clinical study server 104 may store section information including section dependencies for each file of the clinical study data in a table structure (block 228), where the section information may be stored in a study record corresponding to the clinical study.

The clinical study server 104 may index and process each section (block 230). In some embodiments the clinical study server 104 each section is processed by indexing keywords and adding a placeholder tag when a keyword is located in a particular section and the results of the keyword indexing may be stored in an indexed table in the study record. The clinical study server 104 may process each section by normalizing the text of each section to a single structure, including for example, by removing extra spacing and/or special characters.

After normalizing and indexing each section, the clinical study server 104 may parse each section and the indexed keywords for each section to determine a score associated with each section (block 232). The score is based at least in part on the indexed keywords and/or phrases located in the section, where the score corresponds to the likelihood that the particular section is a section required for a formatted clinical study report. In addition, scoring each section may include computing a sense for each word of the section, where each word may have multiple meanings to determine the appropriate meaning for the use of the word in the section.

The score for each section may be analyzed by the clinical study server 104 to determine a probability for each section corresponding to a required section of a clinical study report (block 234). Each section with a highest probability for a required section may be identified as the required section (block 236). Each identified section may be parsed by the clinical study server 104 with one or more routines specific to the identified section to identify clinical study elements that are supposed to be located in the identified section (block 238). For example, the clinical study server may analyze a particular identified section to identify clinical study elements such as a study population, primary endpoint, study objections, number of arms, and/or other such relevant clinical study elements. Based on the identified sections and clinical study elements, the formatted clinical study report may be generated.

Figure 4:
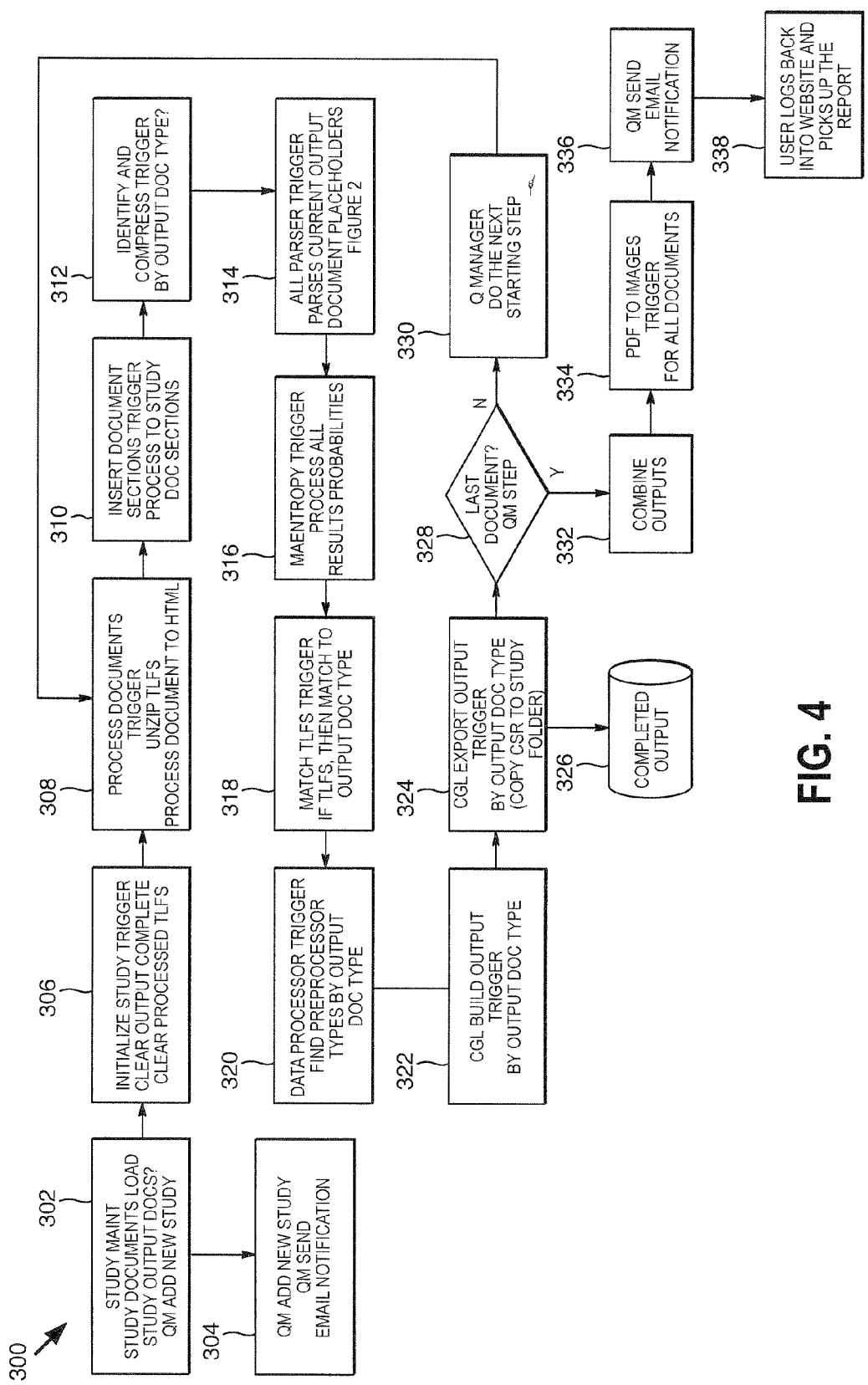
FIG. 4 is a block diagram illustrating a process that may be performed by the user device and/or clinical study server of FIG. 1.

FIG. 4 provides a flowchart illustrating a process 300 that may be performed by a clinical study server to generate a formatted clinical study report. FIG. 4 illustrates the overall operations associated with processing a set of input documents using the clinical study server 104 executing the web interface 144 and the AIE 146 to generate an output document in the form of a formatted clinical study report. In this embodiment, a queue management system is utilized by the clinical study server 104 to trigger the performance of each operation sequentially as shown in the process 300. In some embodiments, the process flow in FIG. 4 may utilize a queue management system with conditional logic. The process 300 begins with the importing the files from a local file system available to the applications (block 302), where an email notification may be communicated to the user (block 304) concurrent with importing the files of the clinical study data. The clinical study server may initialize formatting ('Initialize Study Trigger') by clearing any previously processed data (block 306). The 'ProcessDocuments' operation converts common OpenXML or similar document formats into HTML (block 308). If there are any included compressed files that would include a large numbers of reports, it would decompress those files first, and then convert the document format to HTML.

Once each document is converted to a usable text format may be processed by a 'InsertDocumentSections' process (block 310) that will segregate each files document sections, usually by chapter, then top-level heading, then each sub heading. Standard HTML heading levels may be located in order and each level may be marked and loaded to a Study Document Sections table. This process will keep a relational record of each heading and its parent and child section. Additionally, a copy of each sections HTML will be converted to a normalized text version, removing the HTML tags. In place of HTML tags, localized XML will be placed in the appropriate location for headings. In addition, a keyword indexer table is used to parse each section and if a word or phrase is located, it is marked inside the text inside of XML and it is added to a StudyIndex table that identifies which tags from which placeholder was located for speeding up and reducing errand section identifications (block 312). Additionally, all text is normalized to a single structure, for example, it is not limited but does remove all extra spacing and special characters.

Once the documents are normalized, the 'AIParser' process 350 may begin (block 314). This process begins with looking at which section has previously identified index items associated with the placeholder. The 'AIParser' process will be discussed in further detail with respect to FIG. 5. In addition, the 'Process Placeholder Sections' will be discussed in further detail with respect to FIG. 6. In general, the process takes the identified indexes for a specific placeholder and only looks at those sections, so this in essence may eliminate the need to traverse each section of text.

In the 'AIParser' process, every time a section is evaluated for a phrase it is evaluated based on whether the phrasing must be an exact match or not. So if it identifies an exact match where an exact match was mandatory according to the data model, it moves onto the next phrase to be located, not the next section. So, once it is found, it stops looking. The exact phrases should only be used for highly accurate phrasing that would only be found in the section you are looking to identify. The rest of the phrasing is the semantic phrasing. This phrasing utilizes, but is not limited to, the Michael Lesk algorithm in conjunction with word sensing functions of a dictionary that stems words and builds comparative sensing data. The scoring is computed by taking the sense of each word, which may have multiple meanings, and score single-word and overlap multiple-word phrases to help obtain a total score. This is one iteration of the work and not limited to this. Any preferred scoring mechanism or technique may be used.

Once all sections are scored and then stored in a results table, named here as 'AIResults', the scores of every identified data model per placeholder then may be run through a hidden Markov model that contains all the possible combinations and their likely outcome. Within the data model the probability of a semantic match is grouped by Exact, 99 to 98, 97-96, etc. . . . so that a lower probability against each and every combination is possible to calculate. Within each group an overall percentage of accuracy is assigned. In every identified and calculated score, there is a probability score assigned as being the correct section. These scores are added up and per the identified placeholder-phrase weight is then multiplied by the score and then the totals for the section are added up for an overall score. Then the 'MaxEntropy' process (block 316) tags the highest score as the most likely section to be associated with the placeholder.

Once this is complete, then individual element routines that are specific ('Match TLFs Trigger' block 318 and 'DataProcessor Trigger' block 320), but not limited to, the clinical trial environment can be run to identify clinical study elements, including for example Study Population, Primary Endpoint, Study Objections, Number of Arms, etc. . . . These functions can utilize placeholder objects or in some cases evaluate specifically formatted sections to determine where the data resides. In some cases, this will be a combination of both AI parsing and actual formatting.

Figure 6:
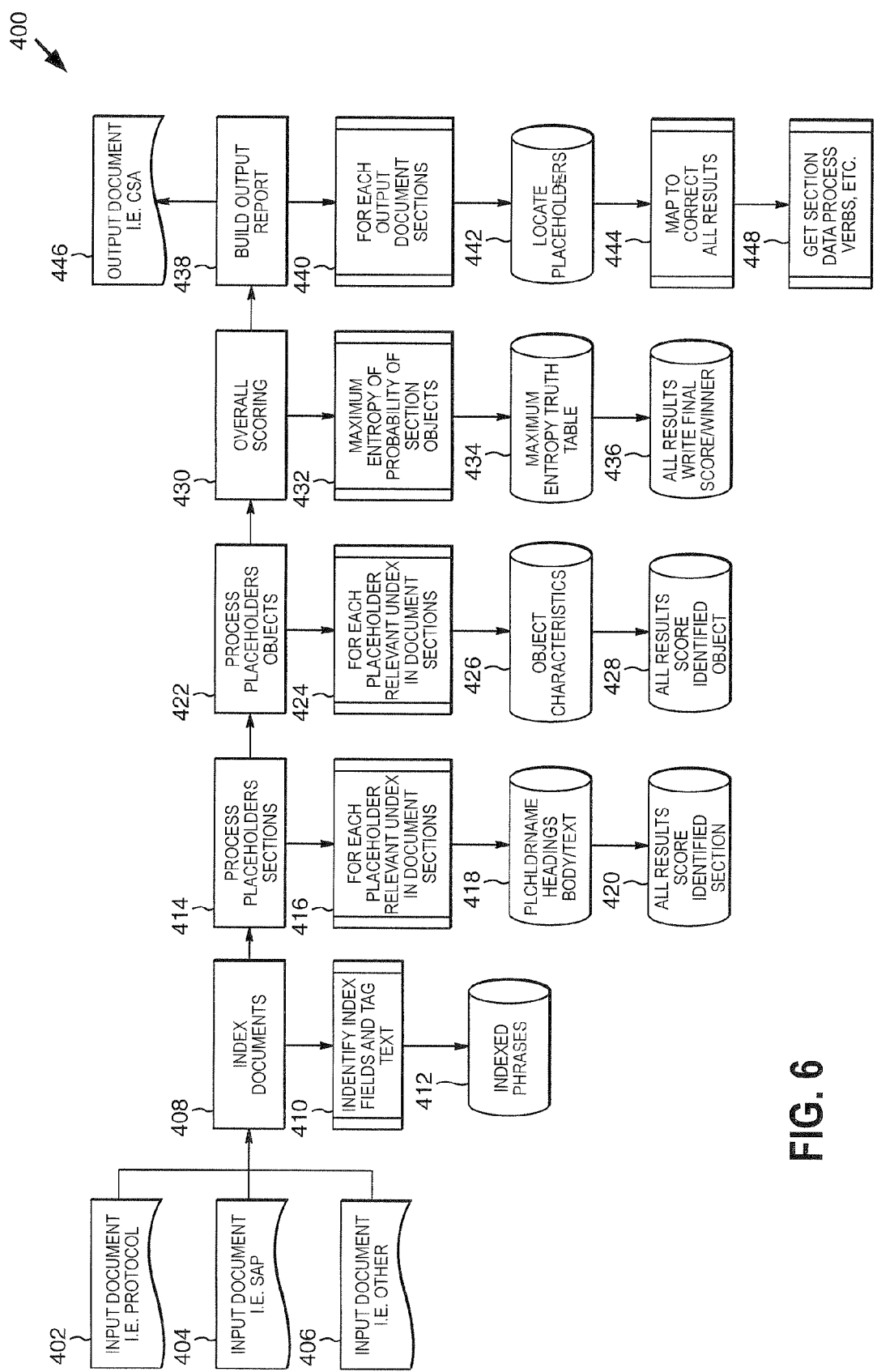
FIG. 6 is a block diagram illustrating a process that may be performed by the clinical study server of FIG. 1 to analyze received clinical study data utilizing placeholders.

The 'BuildOutput' process (block 322) is the culmination placing all of the source document placeholders in one embodiment. FIG. 6 illustrates the creation of placeholders. To use those placeholders, there is a table that has a set of data records associated with the output document type. For example, a Clinical Study Report has a specific file output format. The system stores the HTML formatting for the document in a single or multiple set of data records with placeholders associated with output formatting. For example, if an output of a section for study objectives was identified from a source document, the output may include <body style="font:arial;size:13pt"><xml type="section" name="studyObjectives" style="html" /></body> to have the study objectives that were positively identified display in the appropriate location of the output document. The placeholder data table uses the naming convention of 'studyObjectives' so when it is matched and then later retrieved, it can use that name to lift the text from the original section and output it in the new output document where it belongs. The xml-based placeholders are not limited to, but may contain additional attributes to allow for tagging audit trains; include or excluding sub-sections; including or excluding verb tense changes; including or excluding section number or renumbering; including or excluding existing section headers; and but not limited to formatting and styles within phrases.

Once the 'BuildOutput' process completes, it moves to the 'ExportOutput' process (block 324) to convert the HTML back into the associated document output, including for example the OpenXML format. During this process, the process may perform an additional operation of inserting compliance based or electronic output based formatting. The output may be stored in a database (block 326). If one or more additional files (i.e., documents) have been submitted ("N" branch of block 328), the process 300 may repeat to process the one or more additional files (block 330). However, if all files have been processed ("Y" branch of block 328), the clinical study server 104 may combine all the stored outputs (block 332), convert the format of the combined output to a format for review by the user (block 334), and communicate a notification to the user via email (block 336) such that the user may log in and review the formatted clinical study report (block 338). In some embodiments, at the conclusion of the process, additional steps may be taken to generate PDF files or JPEG files to allow for client review through the web portal application. When the document is completed the customer is notified to review and download the automatically generated document.

Figure 5:
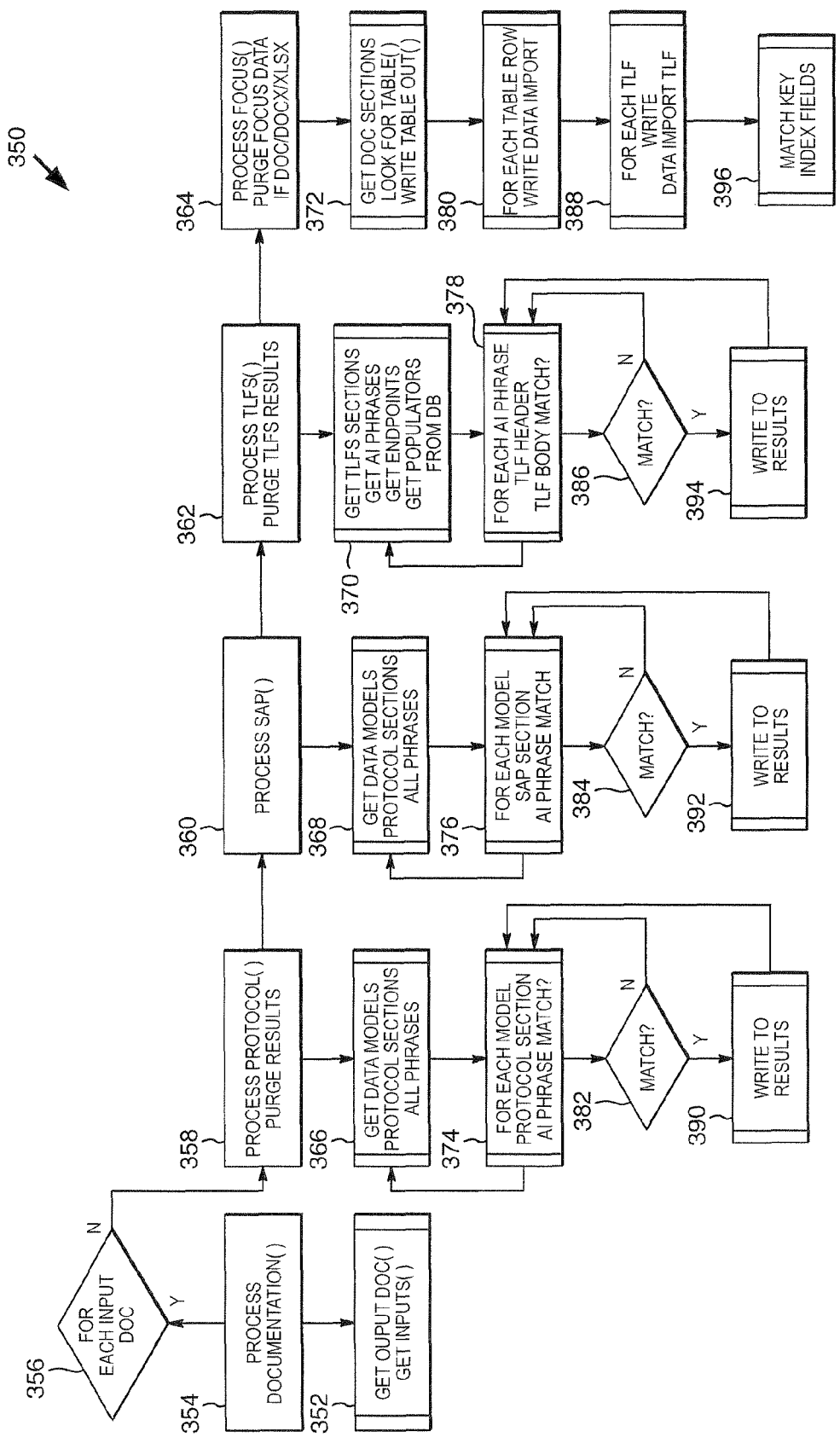
FIG. 5 is a block diagram illustrating a process that may be performed by the clinical study server of FIG. 1 executing an artificial intelligence engine.

FIG. 5 illustrates a process 350 that may be performed by the clinical study server 104 to perform the 'AIParser' process of the process 300 of FIG. 4. As shown, each document input as clinical study data is processed according to FIG. 4 (blocks 352-354). The 'AIParser' loads each document for processing (block 356). In some embodiments, the 'AIParser' may process each document sequentially, or the 'AIParser' may process each document in parallel, where such parallel execution may be accomplished by executing the 'AIParser' using a hyper-threading processor and/or multiple processors. The clinical study server 104 initializes a process to analyze a loaded document (blocks 358-364), and the clinical study server loads any statistical data models and/or key words/phrases associated with the analysis processes (blocks 366-372). For each analysis process and model, the clinical study server 104 parses the document to determine whether sections of the document include matches specified in the particular model (blocks 374-380). Based on the analysis of the document, the results to a match (blocks 382-386) and/or data included in a table of the document (block 388), the clinical study server writes the results to a data structure (blocks 390-396) such as an index table for use generating the formatted clinical study report.

FIG. 6 illustrates a process 400 that may be performed by the clinical study server 104 to generate placeholders for one or more documents included in submitted clinical study data. The documents are loaded (blocks 402-406). The clinical study server 104 indexes the documents (blocks 408-412). Documents may be indexed by locating key phrases to speed up the overall process of analyzing large amounts of text data. If a phrase is identified, the phrase is tagged in the text and such tagging is stored in a table for the document section. The placeholder sections are processed (blocks 414-420). Once indexing is complete, a loop may be executed to analyze all stored placeholders (i.e., tags) to determine an overall score for the section to determine if the section corresponds to a required clinical study section. The scores may be weighted based on what types of matches are identified. The clinical study server 104 may process placeholder objects (blocks 422-428). Objects generally correspond to clinical study elements such as study objectives, end points, a study drug code, a number of arms, and/or other such types of data. Each section may be scored by searching placeholders based on semantic lookup and exact match criteria. Other relevancy factors may be text format or location. The document is scored based on the indexed keywords and/or placeholders (blocks 430-436). Using a max entropy analysis, each section may be scored and the probability of a section and/or object corresponding to a required section/object for a formatted clinical study report is determined. The clinical study server 104 builds an output report (block 438-448), stores the output report and an output document (block 446), and in some embodiments may format the sections (block 448). Each output document may be associated with a document format and required data. The data includes the placeholder by name and any necessary characteristics required in the output. The data may be replaced when generating the formatted clinical study report and the formatted clinical study report is generated.

Figure 7:
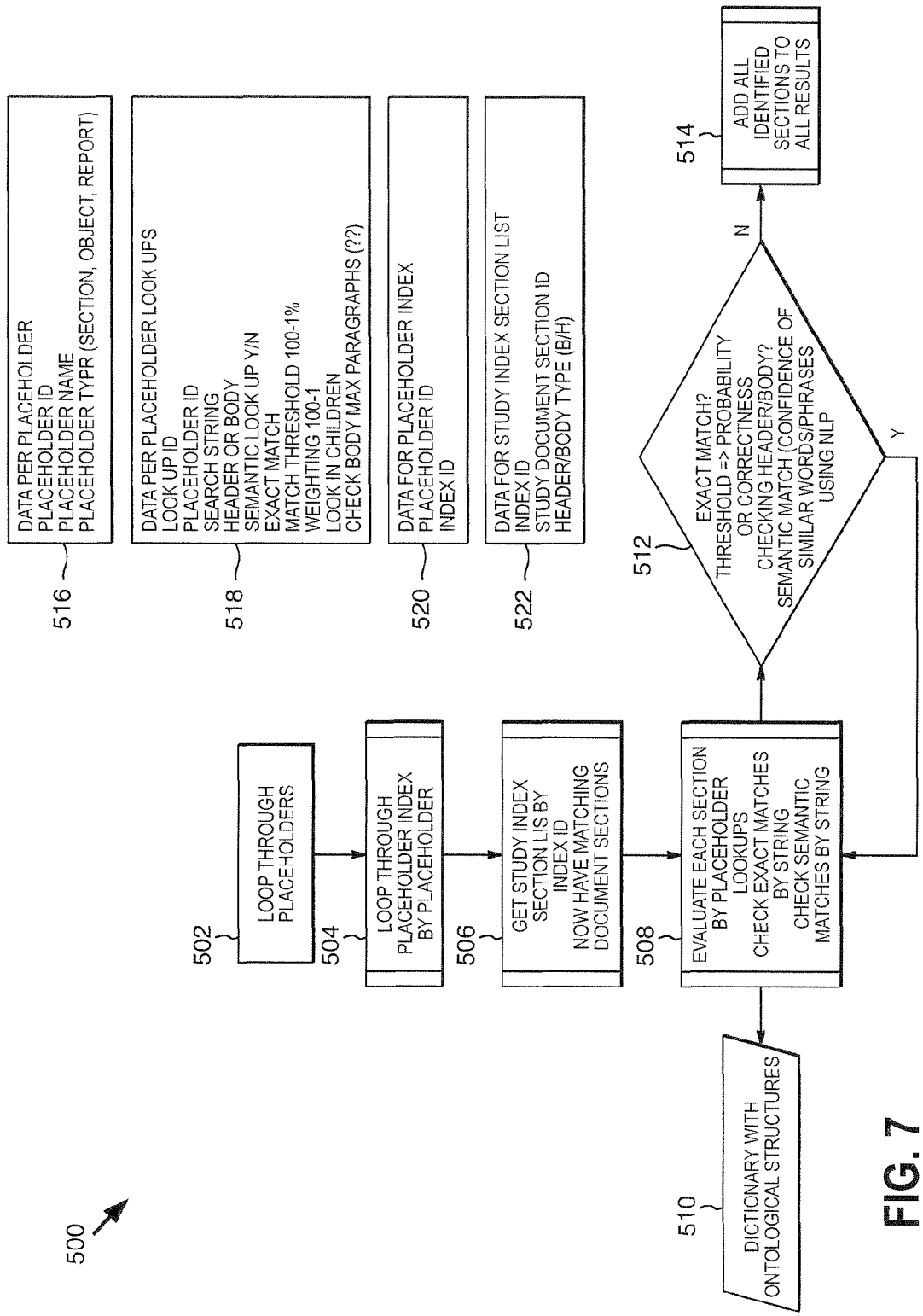
FIG. 7 is a block diagram illustrating a process that may be performed by the clinical study server of FIG. 1 to score sections.

FIG. 7 illustrates a process 500 that may be performed by the clinical study server 104 to score each section of each document submitted for formatting. The clinical study server analyzes each placeholder and the placeholder index (blocks 502-508) to identify placeholders corresponding to sections required for a clinical study report. A dictionary database 510 may be utilized to analyze the ontological structures of the section. If the section includes an exact match and/or exceeds a match threshold, the section is identified as a required section for a clinical study report (blocks 512-514). In such analyses, the placeholders, placeholder lookups, placeholder index, and/or study index section list may include data formatted as shown in the structures 516, 518, 520, 522.

Figure 8:
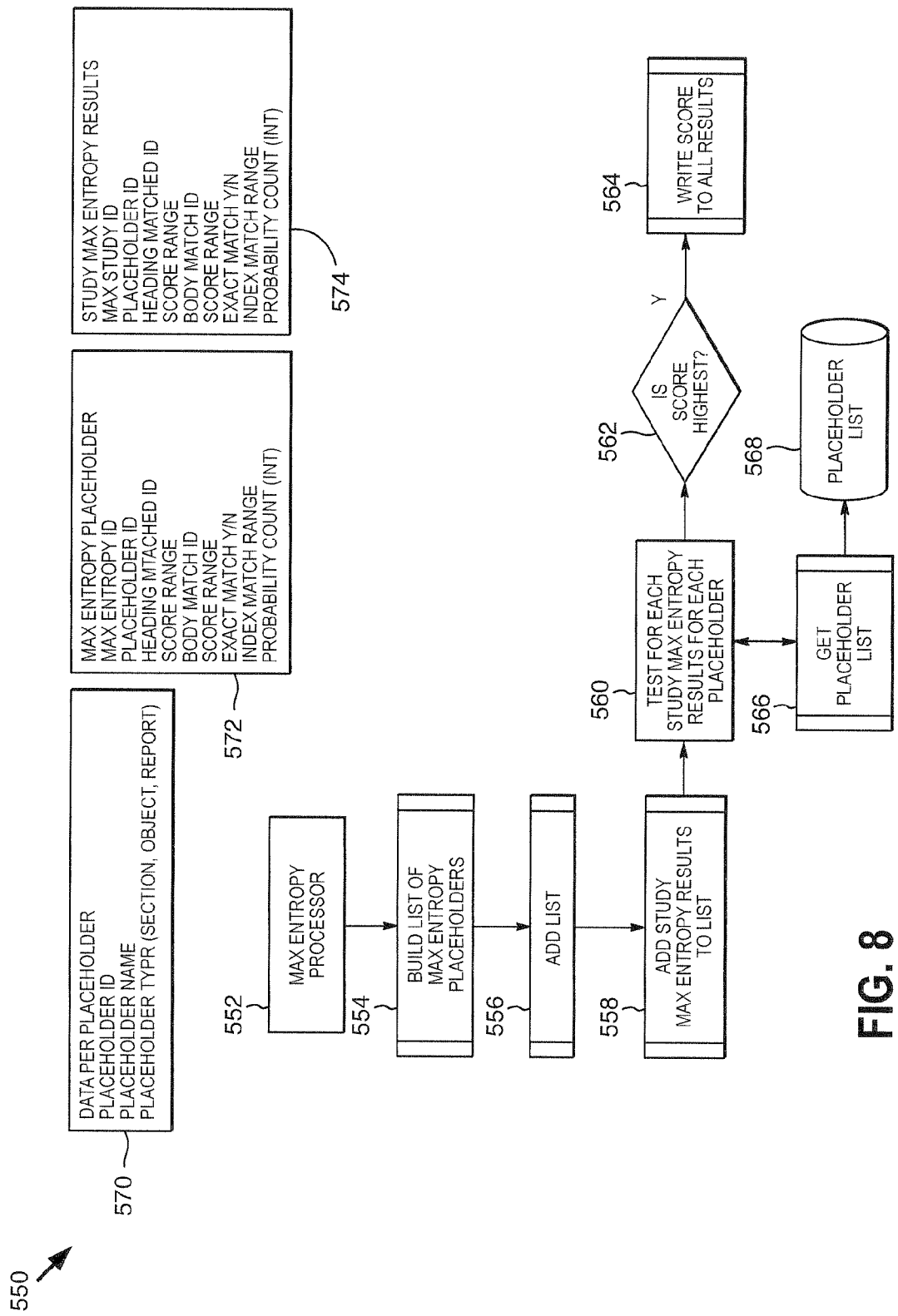
FIG. 8 is a block diagram illustrating a process that may be performed by the clinical study server of FIG. 1 to determine a probability associated with scored sections.

FIG. 8 illustrates a process 550 that may be performed by the clinical study server 104 to perform a max entropy analysis of each section. The clinical study server may execute the max entropy process by building a list of max entropy placeholders, and testing each section based on the indexed section and the max entropy list to determine max entropy results (blocks 552-560). The highest score from the max entropy results for each section is recorded in the 'AI Results' (blocks 562-564) and utilized to generate the formatted clinical study report as shown in FIG. 4. The placeholder list for a section may be retrieved (block 566) from storage 568 during analysis. In such analyses, the placeholders, the max entropy placeholders, and/or the max entropy results may include data formatted as shown in the structures 570, 572, 574, respectively. In embodiments of the invention, the max entropy analysis sets up one or more models based on a placeholder, each maximum entropy/placeholder may be automatically generated by default for every combination, and a probability of correctness may be determined After placeholder sections are identified by semantic comparison and exact comparison, hidden Markov Models may be created from the entries and each identified semantic 'AIResult' may be compared to the max entropy placeholder table. The probability score may be added to the individual 'AIResults' score multiplied by the weight of each identified placeholder score to determine a final score, and the best result may be marked as 'BestScore' so it is used during generation of the output.

While the invention has been illustrated by a description of the various embodiments and the examples, and while these embodiments have been described in considerable detail, it is not the intention to restrict or in any other way limit the scope of the appended claims to such detail. Additional advantages and modifications will readily appear to those skilled in the art. Thus, the invention in its broader aspects is therefore not limited to the specific details, representative apparatus and method, and illustrative examples shown and described. In particular, any of the blocks of the above flowcharts may be deleted, augmented, made to be simultaneous with another, combined, or be otherwise altered or removed in accordance with the principles of the invention. Accordingly, departures may be made from such details without departing from the spirit or scope of this general inventive concept.

What is claimed:
1. A method of automatically generating a clinical study report from a plurality of data files, the method comprising:
   receiving clinical study data including a plurality of data files at a server;
   identifying to said server, a clinical study report, said clinical study report comprising a plurality of elements, each of said elements having an associated phrase and format; and
   a processor of said server:
      converting each of said plurality of data files to a common analysis format;
      locating a plurality of sections within each of said plurality of data files from heading levels within said plurality of data files;
      storing relationship information from said heading levels for said plurality of sections;
      for each of said elements in said clinical study report:
         indexing for each of said plurality of sections, occurrences of said phrase associated with said element within that section;
         identifying any section with a positive index as a possible section for the clinical study report;
         ranking the identified possible sections based on said indexing to provide a probability for each identified possible section to correspond to said element in said clinical study report; and comparing each probability of each identified possible section to determine a best fit section from among the identified possible sections for said element; and generating the formatted clinical study report by reproducing said best fit section for each said element as said element in said clinical study report in said format associated with said element.

2. The method of claim 1, further comprising displaying said formatted clinical study report at a user device in communication with said server.

3. The method of claim 2 further comprising allowing said user device to download said formatted clinical study report from said server only after said user device displayed said formatted clinical study report.

4. The method of claim 1 wherein said comparing uses maximum entropy analysis.

5. The method of claim 1 wherein:
said phrase comprises a keyword;
said identifying identifies any section including said keyword;
said ranking determines a number of occurrences of said keyword in each said identified section; and
said best fit section comprises said identified section with the most occurrences of said keyword.

6. The method of claim 1, wherein said server uses a placeholder to identify each element that does not yet have an associated best fit section.

7. The method of claim 6 wherein the indexing uses semantic similarity to score and identify phrases for building an overall confidence to which each section may have meaning to said placeholder.

8. The method of claim 6 wherein said comparing uses a maximum entropy technique to compare all sections having some meaning to a placeholder to see which section of all identified has the best meaning.

9. The method of claim 1 wherein said common analysis format is HTML.

10. The method of claim 1 wherein each said phrase can only be associated with one said element.

11. The method of claim 1 wherein said indexing is based at least in part on semantics of words included in text of said section.

12. The method of claim 1 wherein said relationship information indicates parent and child relationships between said sections so said indexing can be performed on each section independently or by treating multiple sections having a parent and child relationship with each other as a single section.

* * * * *